Figure 1:
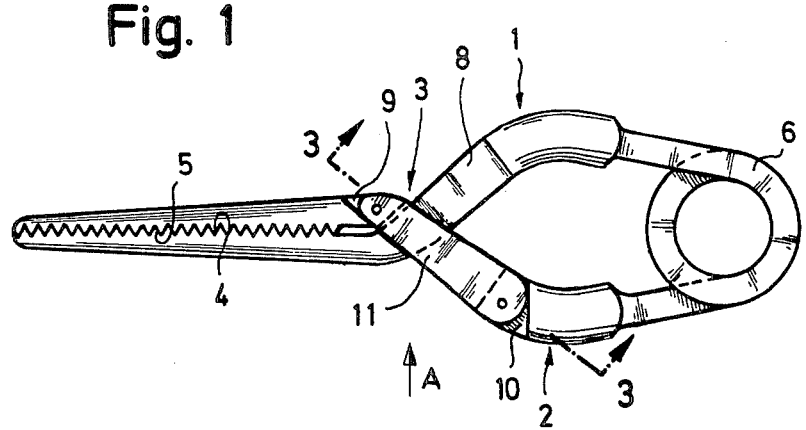

United States Patent [19]

Martin et al.

[11] Patent Number: 4,484,581
[45] Date of Patent: Nov. 27, 1984

[54] ANEURYSM CLIP

[75] Inventors: Fritz Martin, Rietheim-Weilheim; Konrad Laufer, Leibertingen-Altheim; Arnold Ackermann, Rietheim-Weilheim, all of Fed. Rep. of Germany

[73] Assignee: AESCULAP-WERKE AG vormals Jetter & Scheerer, Fed. Rep. of Germany

[21] Appl. No.: 421,967

[22] Filed: Sep. 23, 1982

[30] Foreign Application Priority Data

Oct. 3, 1981 [DE] Fed. Rep. of Germany ....... 3139488

[51] Int. Cl.³ ...................... A61B 17/00; A61B 17/12
[52] U.S. Cl. .................................. 128/346; 128/326; 128/325
[58] Field of Search ................ 128/346, 326, 321, 325

[56] References Cited

U.S. PATENT DOCUMENTS

| | | | |
|---|---|---|---|
| 1,741,457 | 12/1929 | Glass | 128/325 |
| 2,215,725 | 9/1940 | Martinson | 27/23 |
| 2,305,156 | 12/1942 | Grubel | 128/321 |
| 3,598,125 | 8/1971 | Cogley | 128/346 |
| 3,805,792 | 4/1974 | Cogley | 128/346 |
| 3,827,438 | 8/1974 | Kees, Jr. | 128/346 |
| 3,952,749 | 4/1976 | Fridolph et al. | 128/321 |
| 4,024,868 | 5/1977 | Williams | 128/346 |
| 4,360,023 | 11/1982 | Sugita et al. | 128/325 |

FOREIGN PATENT DOCUMENTS

| | | |
|---|---|---|
| 8111068 | of 0000 | Fed. Rep. of Germany. |
| 6935459 | 10/1969 | Fed. Rep. of Germany. |
| 7220437 | 9/1972 | Fed. Rep. of Germany. |
| 2658478 | 11/1978 | Fed. Rep. of Germany. |
| 430945 | 8/1967 | Switzerland. |

OTHER PUBLICATIONS

"DIN 58300", Jan. 1964, Normblätter durch Beush-Vertrieb GmbH, Berlin 15 und Köln.

Primary Examiner—C. Fred Rosenbaum
Assistant Examiner—C. W. Shedd
Attorney, Agent, or Firm—Kenway & Jenney

[57] ABSTRACT

In order to improve the guidance of the arms of an aneurysm clip having two arms crossing each other and pivotably connected and also having a guide means in the area where the two arms cross it is suggested that one arm has a recess in the area where the arms cross, said recess corresponding to the width of the other arm, and that the guide means bridges this recess and is joined to the first arm by spot-welding on either side of the recess.

4 Claims, 3 Drawing Figures

ANEURYSM CLIP

The invention relates to an aneurysm clip as described in the preamble to claim 1.

In the case of known aneurysm clips of this type, which serve to clamp blood vessels and the like and are normally applied with corresponding forcep-type instruments, it is known, with regard to preventing any lateral movement of the two arms away from each other in the area where they cross, to place a ring around the two arms in this area, which may be displaced along the arms when the clip is opened (DE-PS 26 58 478). Although this ring reliably prevents the arms from being pushed laterally apart the manufacture of such a clip is relatively costly since the ring which prevents the arms being forced apart has to be manufactured and mounted as an additional part. In addition, there is the risk that the ring will open and become lost in the area of the operation.

An aneurysm clip avoiding these disadvantages has become known, with which one of the two arms is provided in the area where the arms cross with a tongue extending parallel to this arm. The tongue forms with the arm a groove in this arm which is open towards the back of the clip. The other arm is inserted into this groove when the clip is closed (DE-Gbm 81 11 068.5). Although this solution has proven to be favourable there is still the risk with such a clip that the end of the tongue will damage the surrounding tissue upon insertion.

An aneurysm clip described in the Japanese Utility Model 53-37 505, with which one of the two arms bears a bridge-like spring wire, which extends, in the area where the two arms cross, parallel to one arm and spaced from it so that the other arm is secured against lateral displacement between the spring wire and the one arm in the area where the arms cross. This known construction is, however, extremely complicated since a guide wire has to be bent at its ends in a special way and inserted into special bores in the arm. These bores weaken the arm so that breaks may occur in the area of the bores. In addition, the bridge-like wire protrudes laterally beyond the aneurysm clip so that, on the one hand, the operating surgeon's view is impaired when applying the clip while, on the other hand, there is again the risk of the surrounding tissue being damaged.

The object underlying the invention is to create an aneurysm clip, with which a good guidance of the two arms in the area where the arms cross is guaranteed, the manufacture of which is less costly and with which the risk of damaging the surrounding tissue is lessened.

This object is accomplished according to the invention, for an aneurysm clip of the type stated at the beginning, by the features specified in the characterizing clause of claim 1. The construction according to the invention is particularly favourable in that the guide means bridging the recess may be simply and reliably attached to one arm by spot-welding, for example by laser welding or electron beam welding. Assembly is simplified considerably by this since it is no longer necessary to join the other arm in a complicated manner but is sufficient to insert this other arm laterally into the recess of the first arm and subsequently weld on the bridge-like guide means.

It is also an advantage of this construction that the guide means has the shape of an elongated plate, the ends of which abut flat against plane bearing surfaces of the first arm. The guide means then has a well-defined position and, in addition, does not protrude to the side.

The bearing surfaces are preferably set back relative to the outer profile of the first arm by approximately the thickness of the plate-like guide means so that the surface of the guide means aligns with the surface of the first arm; this will certainly avoid any damage to surrounding tissue.

Provision can also be made for the other arm, which is inserted into the recess of the first arm, to be narrower in the area where the arms cross than to either side of this area. In particular, the depth of the recess in the first arm may be approximately ⅔ of the width of the arm while the other arm is set back in the area where the arms cross by approximately ⅓ of its total width on both sides. The width of the clip along its entire length then corresponds to the width of one arm; it is not wider in the area where the arms cross than to either side of this area.

The guide means according to the invention has very slight frictional losses since the two arms may slide along each other almost without friction. This enables an exactly defined closing pressure to be set. Due to the construction according to the invention structural changes in the material will also be avoided, which could otherwise lead to a weakness.

Figure 2:
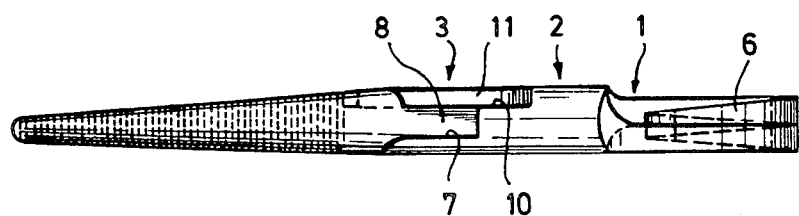

The following description of a preferred embodiment of the invention serves, in conjunction with the drawings, to explain the invention in detail. The drawings show:

FIG. 1 a side view of the aneurysm clip according to the invention;

FIG. 2 a plan view of the clip in the direction of arrow A in FIG. 1 and

Figure 3:
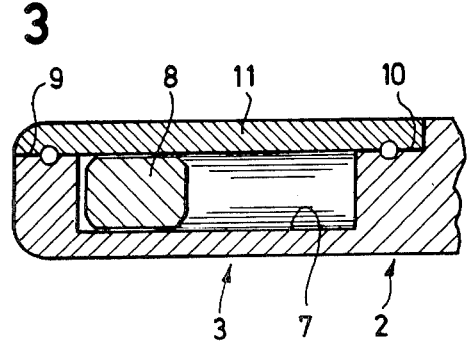

FIG. 3 a sectional view along line 3—3 in FIG. 1.

The invention relates in general to vessel clamps for surgical use; the present embodiment describes in particular a clip for neurosurgical purposes, for example for clamping aneurysms. This clip has two arms 1 and 2 crossing each other in the area 3; these arms have at one end plane clamping surfaces 4, 5 which face each other, their surfaces, in the illustrated embodiment, being serrated transversely to the longitudinal direction of the arms. The individual peaks and valleys of this surface of adjacent clamping faces fit complementarily into each other.

In the area 3 where the arms cross, which is immediately adjacent to the clamping faces 4 and 5, the two arms 1 and 2 diverge and are finally connected with each other at the end of the clip via a double coil 6. The clip consists of spring wire so that, due to the construction of the double coil at the end of the clip, the two arms will be elastically pushed apart in the adjacent area and the clamping faces 4, 5 pressed elastically against each other.

The first arm 1 has, in the area 3 where the arms cross, a recess 7 open towards the other arm 2, the depth of this recess being approximately ⅔ of the entire width of the first arm (FIG. 3). This recess extends over the entire length of the area 3 where the arms cross.

The other arm is, for the entire area where the arms cross, set back on both sides relative to its normal width, in the illustrated embodiment by about ⅓ of its entire width on each side (FIG. 2). This also extends over the entire area where tha arms cross. The connection crosspiece 8 between those parts of arm 2 located to either side of the area where the arms cross is inserted into the recess 7, as shown in FIG. 3. The width of the connection crosspiece 8 then corresponds approximately to the depth of the recess 7.

The first arm 1 has at both ends of the recess 7 plane bearing surfaces 9, 10 (FIG. 3), on which the ends of an elongated, plate-like guide element 10 lie flat, this guide element bridging the recess 7. In the bearing area guide element 11 and arm 1 are joined together by spot-welding, for example by laser welding or electron beam welding, so that the recess 7, with the connection crosspiece 8 disposed therein, is closed towards the outside, as shown in FIG. 3. The bearing faces 9 and 10 are preferably set back relative to the outer profile of the arm 1 by the thickness of the guide element 11 so that the surface of the guide element aligns with the surface of the arm.

The relative displacement of the two arms in the area where they cross is in no way hindered by the guide element 11 bridging the recess 7. It is, however, reliably ensured that the arms may move apart transversely to the plane of the clip.

We claim:

1. Aneurysm clip comprising two arms formed of a continuous length of a resilient structural material that cross each other and are resiliently connected by spring means that is also part of said continuous length of resilient structural material, said arms bearing on their free ends opposed clamping surfaces which are pressed resiliently against each other by said spring means pivoting the arms apart in a plane in the area behind their cross-over point, and further comprising a guide means in the area where the two arms cross, said guide means including a guide plate extending parallel to one arm in the area where the arms cross and maintaining such a distance from said one arm that the other arm is guided between said guide plate and the first arm so that the two arms cannot move apart perpendicular to said plane defined by the arms in the area where they cross vertically to the plane defined by the arms, said first arm (1) having a first recess in the area (3) where the arms cross to define a pair of planar bearing surfaces (9,10) that are set back relative to the outer profile of said one arm (1) by substantially the thickness of said guide plate (11), and said first arm (1) also having a second recess (7) corresponding to the width of the other arm (2), said guide plate (11) bridging said second recess (7) with the faces of the end portions of said guide plate each resting flatly on one of said bearing surfaces (9,10) and means for fixedly attaching said guide plate end portions to said bearing surfaces.

2. Aneurysm clip according to, claim 1 characterized in that the other arm (2) inserted into said second recess (7) of the first arm (1) is narrower in the area where the arms cross than to either side of this area.

3. Aneurysm clip according to claim 2, characterized in that the depth of the recess (7) in the first arm (1) is approximately $\frac{2}{3}$ of the width of said arm (1), and that the other arm (2) is set back in the area where the arms cross by approximately $\frac{1}{3}$ of its entire width on both sides.

4. Aneurysm clip according to claim 1 wherein said attaching means comprises at least one spot weld at each of said end portions of said guide plate (11).

* * * * *